(12) United States Patent
Pullagurla et al.

(10) Patent No.: US 8,952,148 B2
(45) Date of Patent: Feb. 10, 2015

(54) PROCESS FOR THE PREPARATION OF TAUROLIDINE AND ITS INTERMEDIATES THEREOF

(75) Inventors: Manik Reddy Pullagurla, Hyderabad (IN); Jagadeesh Babu Rangisetty, Hyderabad (IN); Neelam Naidu Dokula, Vizianagaram (IN)

(73) Assignee: Biophore India Pharmaceuticals Pvt Ltd, Hyderabad (IN)

( * ) Notice: Subject to any disclaimer, the term of this patent is extended or adjusted under 35 U.S.C. 154(b) by 0 days.

(21) Appl. No.: 13/883,367

(22) PCT Filed: Nov. 18, 2011

(86) PCT No.: PCT/IN2011/000805
§ 371 (c)(1),
(2), (4) Date: May 3, 2013

(87) PCT Pub. No.: WO2012/070066
PCT Pub. Date: May 31, 2012

(65) Prior Publication Data
US 2013/0237700 A1    Sep. 12, 2013

(30) Foreign Application Priority Data
Nov. 23, 2010  (IN) .......................... 3513/CHE/2010

(51) Int. Cl.
*C07D 285/18*    (2006.01)
*A61K 31/549*    (2006.01)

(52) U.S. Cl.
CPC ............ *C07D 285/18* (2013.01); *A61K 31/549* (2013.01)
USPC ........................................... 544/8; 514/222.5

(58) Field of Classification Search
USPC ............................................................. 544/8
See application file for complete search history.

(56) References Cited

U.S. PATENT DOCUMENTS 2,184,279 A    12/1939   Christiansen
3,423,408 A    1/1969    Pfirrmann

FOREIGN PATENT DOCUMENTS

CH         482713 A        12/1969
EP         0 863 133 A2    9/1998
WO         WO-2011/107283 A2   9/2011

OTHER PUBLICATIONS

International Search Report for PCT/IN2011/000805, mailed Apr. 3, 2012; ISA/AU.

*Primary Examiner* — Kahsay Habte

(57) ABSTRACT

The present invention relates to a process for the preparation of substantially pure Taurolidine.

5 Claims, No Drawings

PROCESS FOR THE PREPARATION OF TAUROLIDINE AND ITS INTERMEDIATES THEREOF

BACKGROUND

Taurolidine is an antibacterial drug and also has antiendotoxic substance, which is used as an antiseptic solution in surgery for washing out the abdominal cavity and it also prevents septic shock. It is commercially sold as Taurolidine (Formula I). The present invention relates to a process for the preparation of Taurolidine which provides significant advantages over the existing processes.

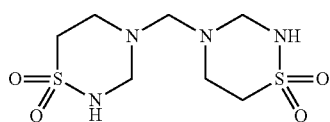

Formula I

SUMMARY OF THE INVENTION

The following patents and applications describe the synthesis of Taurolidine

CH482713 describes the first synthesis of Taurolidine by reacting Taurinamide HCl with 1.5 eq of formaldehyde. One of the major drawbacks of this synthesis is the carry over of the chloride ions to the final stage, which has a stringent specification of NMT 500 ppm in the finished product. It is cumbersome to purify the product devoid of any chloride ions.

EP0863133 describes a process for the preparation of Taurinamide from beta-aminoethanesulfonylazide. Handling of organic azides at commercial scale is highly risky as azides are explosive in nature.

U.S. Pat. No. 2,184,279 describes a process for the preparation of taurinamide from phalimide protected Taurine.

The process described in this patent utilizes hydrazine hydrate for the deprotection of the pthalimide group. The deprotection process usually works well at lab scale and it results in poor yields when performed at commercial scale. Moreover product obtained is difficult to separate from the hydrazine residuals.

Apart from the above said disadvantages, synthesis of Taurolidine at industrial level suffers significant drawbacks discussed subsequently. Therefore there is a need in the art for a simple and most efficient procedure for the synthesis of Taurolidine.

Cbz-taurine (II) is a potential intermediate for the synthesis of Taurolidine. It is highly soluble in water posing difficulties in the isolation procedures. The most efficient way for its isolation known in the art involves water distillation. The sodium salt of Cbz-taurine have earlier been isolated by lyophilization as reported in Tetrahedron 52, 15, 5591 or by complete water distillation as reported in Bioorganic Chemistry 2001, 29, 6, 357.

In one embodiment, the current invention suggests an alternate procedure for isolation of Cbz-taurine without distillation or continuous extraction, and which is viable at a large scale.

Cbz-Taurinamide (III), another crucial intermediate is converted to a HCl salt—Taurinamide hydrochloride and subsequently to Taurolidine as described in CH482713. This prior art process of hydrochloride salt formation and its conversion to Taurolidine, however, resulted in significant amounts of chloride impurities, which involved tedious workups for the purification.

In another aspect of the invention, an organic acid salt formation is employed for the conversion of Taurinamide to Taurolidine, wherein the chloride ions are totally avoided. Interestingly, this process resulted in increased yields compared to other prior art procedures, which do not involve salt formation.

The final product Taurolidine decomposes during recrystallization procedures posing great difficulties in its purification. None of the prior art references suggest purification procedures without the decomposition of the compound and in substantially pure form.

In one aspect of the invention, Taurolidine is purified without decomposition to obtain a highly pure compound, whose purity is not less than 99.5%.

DETAILED DESCRIPTION OF THE INVENTION

The current process for the preparation of Taurolidine is depicted in Scheme 1

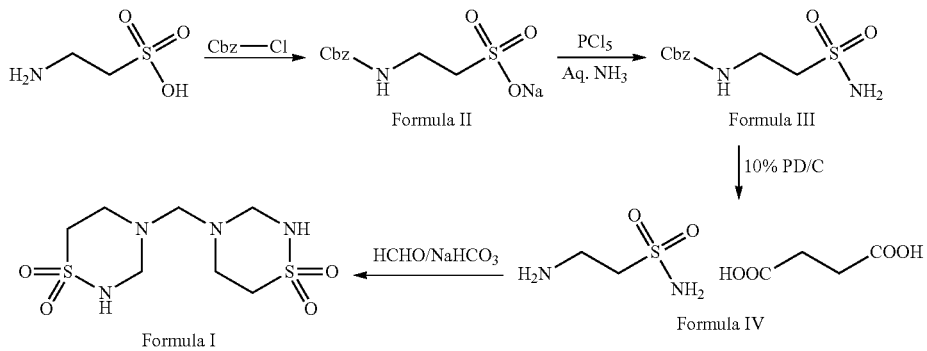

Cbz-taurine is highly soluble in water posing difficulties in the isolation procedures. The present invention provides a simple process to isolate it as a sodium salt from the reaction mixture. The reaction is performed in the presence of sodium hydroxide and once the reaction is completed, the pH of the reaction is adjusted to make it highly basic (pH 12-14) to isolate the corresponding sodium salt of Cbz-taurine. Subsequent cooling results in the precipitation of the product thus avoiding the usage of any solvents or continuous extraction.

The product precipitated is collected by filtration.

The invention also provides a process for the conversion of Cbz-taurine sodium salt to Cbz-Taurinamide in presence of $PCl_5$, $POCl_3$ or $SOCl_2$ followed by the treatment of ammonia; $PCl_5$ being the most preferred reagent.

Cbz-taurinamide formed is subjected to hydrogenation in presence of palladium catalyst to obtain Taurinamide which is subsequently converted to Taurinamide salt.

The prior art procedures for the conversion of Taurinamide to Taurolidine involve the intermittent Taurinamide hydrochloride salt. The Taurinamide hydrochloride salt resulted in high concentration of chloride content in the final product and attempts to purify the product resulted in significant loss in the yield.

In the present invention several organic acid salts of Taurinamide were synthesized. Interestingly it was found that organic acid salts like oxalate, citrate, fumarate, maleate, malate and succinate yielded purer Taurolidine over the inorganic acid salts, succinate being the most suitable salt for the conversion.

The final product Taurolidine decomposes during recrystallization procedures posing great difficulties in its purification. It was found that alcoholic solvents and water are most unsuitable for the recrystallization and significant amount of the compound decomposes in these solvents, thereby reducing the final yield quantitatively. None of the prior art references suggest purification procedures without the decomposition of the compound and in substantially pure form.

The present inventors thus propose an industrially viable procedure for isolation of Taurolidine in substantially pure form.

Taurolidine is dissolved in a suitable solvent to obtain a clear solution. The product starts to precipitate and an anti solvent is added optionally to maximize the precipitation procedure. The solvents employed for the purification are non-aqueous aprotic solvents comprising DMSO, DMAc, DMF, Acetonitrile, DMSO being the most preferred solvent. The antisolvents employed are toluene, ethyl acetate, dichloromethane, ether; toluene being the most preferred.

Taurolidine obtained by the instant procedure has purity greater than or equal to 99.5%.

The process of the invention is illustrated by the following examples to obtain Taurolidine.

Example I

Cbz-Taurine Sodium Salt (Formula II)

To 1000 ml of water in the RBF charge 192 gm of (3.0 eq) of sodium hydroxide under cooling followed by 200 gm of Taurine and dissolve it until clear solution is obtained. Cool to 0° C. to 5° C., and Charge 50% CBZ-Cl in toluene at 0° C. to 5° C. After completion of addition, maintain at room temperature for 14 h. Separate the toluene layer and wash the aqueous layer with 2×200 ml of ethyl acetate. Add slowly 27 gm of sodium hydroxide in 60 ml of water to the aqueous layer and adjust pH to 12-14. Cool to 0° C. to 5° C. and a white solid separates from the solution. Filter the solid and dry the solid at 60-70° C. Weight of the solid: 320 g Example 2

Cbz-Taurinamide (Formula III)

To a clean dry flask charge 1500 ml of toluene and charge 320 gm of Formula II and cool to 0° C. to 5° C. Charge 308 gm of $PCl_5$ slowly at 0° C. to 5° C. for 2 hrs. Maintain at 0° C. to 5° C. up to completion of reaction. Quench the RM into another flask containing 2 ltr of water at 0° C. to 5° C. Separate the organic layer, wash and extract the aqueous layer with toluene. Dry the organic layer with sodium sulphate and cool to 0° C. to 5° C. Purge ammonia gas into the reaction mass till the reaction is complete. Filter the solid and dissolve the solid in 2 ltr of water and extract the aqueous layer with 2×600 ml of ethyl acetate. Dry the organic layer with sodium sulphate and concentrate it under reduced pressure to obtain a white solid. Weight of the solid: 150 g Example 3

Taurinamide Succinate (Formula IV)

Take a suspension of 100 g of Cbz-Taurinamide in 1000 ml methanol, and 10% Pd/C (1.0 g) and subject to hydrogenation at 45-50 psi. Upon completion of the reaction filter the catalyst and add succinic acid (1.0 eq) to the solvent and distill off the solvent under vacuum to provide the title compound in about 90% yield as a white solid.

Example 4

Taurolidine (Formula I)

To a solution of 100 g Taurinamide succinate in water is added sat sodium bicarbonate solution and pH adjusted to 7-8. To the solution was added formaldehyde (50 ml) and allowed to stir for 4 h. The solid obtained was filtered and washed with water to give Taurolidine. The title compound was obtained in about 70% yield and about 98% purity.

Example 5

Purification of Taurolidine

Taurolidine (100 g) was dissolved in DMSO (400 ml) and a clear solution is obtained and a precipitate is obtained immediately. The solid is filtered and washed with toluene and dried to give a white solid in 40% yield. The product obtained was >99.5% pure.

Example 6

Purification of Taurolidine

Taurolidine (100 g) was dissolved in DMSO (400 ml) and a clear solution is obtained and a precipitate is obtained immediately. To the solution, toluene (1000 ml) is added. The solid is filtered and washed with toluene and dried to give a white solid in 70% yield. The product obtained was >99.5% pure by HPLC and passed elemental analysis within 0.4% of the theoretical values.

Example 7

Purification of Taurolidine

Taurolidine (100 g) was dissolved in DMAc (800 ml) and to the solution, toluene (1000 ml) is added. The solid is filtered and washed with toluene and dried to give a white solid in 70% yield.

We claim:
1. Process for the preparation of Taurolidine which comprises:
   a. Reaction of Taurine and Cbz-cl in the presence of aqueous sodium hydroxide and toluene as solvent
   b. Separation of Cbz-taurine sodium salt precipitated out
   c. Conversion of Cbz-taurine sodium to Cbz-Taurinamide in the presence of $PCl_5$ followed by treatment with ammonia
   d. Conversion of Cbz-Taurinamide to taurinamide in presence of Pd/C followed by in situ generation of Taurinamide Succinate by reaction of Taurinamide and succinic acid
   e. Treatment of Taurinamide succinate with formaldehyde under basic conditions to generate Taurolidine.
2. Process for the purification of Taurolidine which involves
   a. dissolving Taurolidine in non-aqueous aprotic solvents to obtain clear solution
   b. isolation of the pure compound which precipitates from the clear solution.
3. Process of claim 2, wherein the non-aqueous aprotic solvents are DMSO, DMAc, DMF, Acetonitrile.
4. Process of claim 2 wherein the purification stage has an additional step of adding antisolvent.
5. Process of claim 4, wherein the anti solvents are toluene, ethyl acetate, diethyl ether and dichloromethane.

\* \* \* \* \*